United States Patent

Jegham et al.

Patent Number: 6,143,772
Date of Patent: *Nov. 7, 2000

[54] COMPOUNDS DERIVED FROM 3-(BENZOFURAN-5-YL)OXAZOLIDIN-2-ONE, PREPARATION METHOD THEREFOR AND THERAPEUTICAL USE THEREOF

[75] Inventors: Samir Jegham, Argenteuil; Frederic Puech, Rueil Malmaison; Philippe Burnier, Maisons Laffitte; Danielle Berthon, Mareil Marly, all of France

[73] Assignee: Synthelabo, Le Plessis Robinson, France

[ * ] Notice: This patent issued on a continued prosecution application filed under 37 CFR 1.53(d), and is subject to the twenty year patent term provisions of 35 U.S.C. 154(a)(2).

[21] Appl. No.: 09/066,365
[22] PCT Filed: Nov. 5, 1996
[86] PCT No.: PCT/FR96/01731
§ 371 Date: May 8, 1998
§ 102(e) Date: May 8, 1998
[87] PCT Pub. No.: WO97/17346
PCT Pub. Date: May 15, 1997

[30] Foreign Application Priority Data

Nov. 9, 1995 [FR] France ................................ 95 13256

[51] Int. Cl.⁷ .......................... A61K 31/42; A61P 25/24; A61P 25/18; C07D 263/16; C07D 413/04
[52] U.S. Cl. .......................... 514/376; 548/231; 548/232
[58] Field of Search ................... 548/231, 232; 514/376

[56] References Cited

U.S. PATENT DOCUMENTS

| | | | |
|---|---|---|---|
| 3,654,298 | 4/1972 | Douzon et al. | 548/232 |
| 4,250,318 | 2/1981 | Dostert et al. | 548/232 |
| 4,259,338 | 3/1981 | Paioni et al. | |
| 4,461,773 | 7/1984 | Gregory | 548/232 |
| 4,476,136 | 10/1984 | Dostert et al. | 514/376 |
| 4,517,197 | 5/1985 | Ancher et al. | 514/376 |
| 5,036,090 | 7/1991 | Jarreau et al. | 514/376 |
| 5,036,091 | 7/1991 | Jarreau et al. | 514/376 |
| 5,171,747 | 12/1992 | Jarreau et al. | 514/376 |
| 5,196,543 | 3/1993 | Jarreau et al. | 548/232 |
| 5,235,063 | 8/1993 | Jarreau et al. | 548/232 |
| 5,684,023 | 11/1997 | Riedl et al. | 548/231 |

FOREIGN PATENT DOCUMENTS 44 25 609  1/1996  Germany.

*Primary Examiner*—Mukund J. Shah
*Assistant Examiner*—Brenda Coleman
*Attorney, Agent, or Firm*—Jacobson, Price, Holman & Stern, P.L.L.C.

[57] ABSTRACT

Compounds derived from 3-(benzofuran-5-yl) oxazolidin-2-one, of general formula (I)

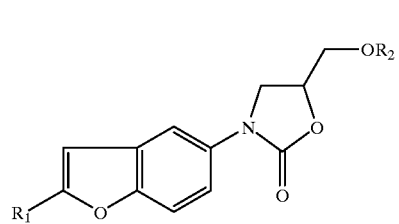

in which:

$R_1$ represents a phenyl group, a phenylmethyl group, an alkyl group or a fluoroalkyl group, and $R_2$ represents a hydrogen atom or a methyl group. Application in therapeutics.

10 Claims, No Drawings

COMPOUNDS DERIVED FROM 3-(BENZOFURAN-5-YL)OXAZOLIDIN-2-ONE, PREPARATION METHOD THEREFOR AND THERAPEUTICAL USE THEREOF

This application is a national stage entry under 35 U.S.C. 371 of PCT/FR96/01731 filed Nov. 5, 1996.

The present invention relates to compounds derived from 3-(benzofuran-5-yl)oxazolidin-2-one, a process for their preparation and their application in therapeutics.

The compounds of the invention correspond to the general formula (I)

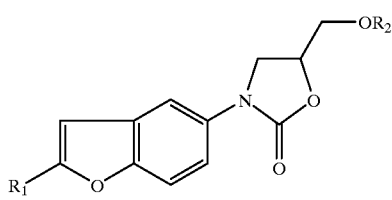

(I)

in which:

R$_1$ represents a phenyl group, a phenylmethyl group, an alkyl group comprising 3 to 6 carbon atoms or a fluoroalkyl group comprising 1 to 6 carbon atoms, and R$_2$ represents a hydrogen atom or a methyl group.

In the context of the present invention:

an alkyl group is an aliphatic, saturated, linear or branched group, a fluoroalkyl group is an alkyl group such as defined above, of which at least one of the carbon atoms is substituted by one or more fluorine atoms.

Usually, a fluoroalkyl group according to the invention comprises 3 fluorine atoms substituted onto the carbon atom at the end of the alkyl chain.

The compounds of formula (I) have an asymmetric carbon atom. They can thus exist in the form of enantiomers. The invention comprises the pure enantiomers as well as their mixtures, including their racemic mixtures.

Preferred compounds of formula (I) are those for which (i) R$_1$ represents a phenyl group, a phenylmethyl group, a propyl group or a 3,3,3-trifluoropropyl group and/or (ii) R$_2$ represents a methyl group.

The compounds of formula (I) can be prepared according to the process represented in the annexed scheme 1, starting from a compound of formula (II)

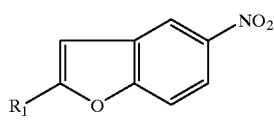

(II)

in which R$_1$ is defined as in the formula (I).

This process consists in reducing the nitro group of the compound of formula (II), in reacting the compound of formula (III)

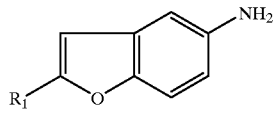

(III)

with ethyl chloroformate and sodium bicarbonate to obtain the compound of formula (IV)

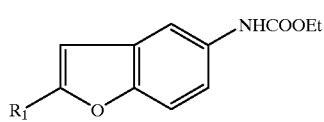

(IV)

where Et is an ethyl group and R$_1$ is as defined above. The compound of formula (IV) can then be reacted with 4-methoxymethyl-1,3-dioxolan-2-one to prepare the compounds of formula (I) where R$_2$ is a methyl group. Then, said compound of formula (I) where R$_2$ is a methyl group can be treated with boron tribromide to obtain the compounds of formula (I) where R$_2$ is a hydrogen atom.

The compounds of formula (II) can be prepared according to the process represented in scheme 2 below:

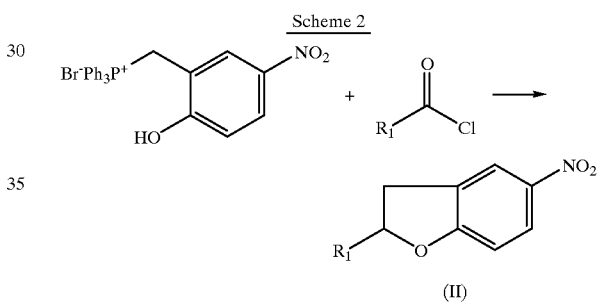

Scheme 2 which consists in treating (2-hydroxy-5-nitrophenyl)-methyltriphenylphosphonium bromide (compound described in Chem. Ber. 1986, 119, 2169) with an acid chloride of formula R$_1$COCl in which R$_1$ is defined as in the formula (I).

The 5 (R) and 5 (S) isomers of the compounds of formula (I) are prepared by reaction of a compound of formula (IV) with the 4 (S) and 4 (R) isomers of 4-methoxymethyl-1,3-dioxolan-2-one respectively.

4 (S)-Methoxymethyl-1,3-dioxolan-2-one is a known compound whose preparation is described in U.S. Pat. No. 5,264,443.

4 (R)-Methoxymethyl-1,3-dioxolan-2-one is prepared according to the same method, starting from (R)-2,2-dimethyl-1,3-dioxolan-4-methanol.

The following examples illustrate the present invention.

EXAMPLE 1

3-[2-(3,3,3-trifluoropropyl)benzofuran-5-yl]-5 (R)-methoxymethyloxazolidin-2-one 1.1. 2-(3,3,3-Trifluoropropyl)-5-nitrobenzofuran A suspension of 4.0 g (8.1 mmol) of (2-hydroxy-5-nitrophenyl) methyltriphenylphosphonium bromide in 50 ml of toluene is heated to reflux, then 5.1 ml (36 mmol) of triethylamine and 1.9 g (12 mmol) of 4,4,4-trifluorobutyryl chloride are added. The mixture is stirred for 2 hours, then it is filtered and the filtrate is concentrated under reduced pressure. By chromatography of the residue on a silica column using a 0–30% mixture of dichloromethane in cyclohexane, 1.1 g of product are obtained. Melting point: 70–71° C.

1.2. 5-Amino-2-(3,3,3-trifluoropropyl)benzofuran

A mixture of 2.4 g (9.2 mmol) of 2-(3,3,3-trifluoropropyl)-5-nitrobenzofuran, 0.65 g (17 mmol) of sodium borohydride, 45 mg of Adogen® 464 (methyl trialkylammonium chloride) and 0.38 g of 5% palladium on carbon containing 50% of water in 95 ml of dichloromethane and 48 ml of water is stirred for 5 hours, then it is filtered on silica and the silica is rinsed with ethanol. The filtrate is then concentrated under reduced pressure and coevaporated with toluene. By chromatography of the residue on a silica column using a 0–30% mixture of ethyl acetate in cyclohexane, 2.0 g of product are obtained. Melting point: 74° C.

1.3. 5-Ethoxycarbonylamino-2-(3,3,3-trifluoropropyl)-benzofuran

A solution of 2.0 g (8.7 mmol) of 5-amino-2-(3,3,3-trifluoropropyl) benzofuran in 30 ml of a 9/1 mixture of tetrahydrofuran and water is reacted for 30 min with 0.92 ml (9.6 mmol) of ethyl chloroformate in the presence of 1.1 g (13 mmol) of sodium hydrogen-carbonate. The reaction mixture is then diluted with water and dichloromethane, and then the organic phase is separated, dried over sodium sulfate and concentrated under reduced pressure. 2.5 g of product are obtained. Melting point: 108° C.

1.4. 3-[2-(3,3,3-Trifluoropropyl)benzofuran-5-yl]-5(R)-methoxymethyloxazolidin-2-one A solution of 1.2 g (4.0 mmol) of 5-ethoxycarbonylamino-2-(3,3,3-trifluoropropyl) benzofuran in 16 ml of dimethylformamide is reacted for 4 hours with 700 mg (5.2 mmol) of 4(S)-methoxymethyl-1,3-dioxolan-2-one added by fractions, in the presence of 55 mg (0.40 mmol) of potassium carbonate. The mixture is then poured into water, the product is extracted with diethyl ether, and then the organic phase is washed with water, dried over sodium sulfate and concentrated under reduced pressure. By chromatography of the oil obtained on a silica column with a 0–30% mixture of ethyl acetate in cyclohexane and recrystallization in a mixture of diisopropyl ether and diethyl ether, 1.05 g of product are obtained. Melting point: 79.9–80.0° C. $[\alpha]_D^{20}=-36.9°$ (c=1; dichloromethane).

EXAMPLE 2

3-[2-(3,3,3-trifluoropropyl)benzofuran-5-yl]-5(S)-methoxymethyloxazolidin-2-one 2.1. 4(R)-Methoxymethyl-2,2-dimethyl-1,3-dioxolane In a 6 liter reactor equipped with a condenser, a temperature probe and a dropping funnel are introduced 420 ml of demineralized water and 420 g (10.5 mol) of sodium hydroxide in pellets. To the solution, stirred at 20° C., are added 2.3 l of dichloromethane, 396 g (3.00 mol) of (R)-2,2-dimethyl-1,3-dioxolane-4-methanol ($[\alpha]_D^{20}=-11°$; c=4; methanol) and 20.5 g (0.090 mol) of benzyltriethylammonium chloride. 567 g (4.50 mol) of dimethyl sulfate are then added in 50 min, while keeping the temperature below 30° C. The mixture is stirred for 18 hours and then 1 liter of water is added. The organic phase is separated and washed with 0.5 l of water. The aqueous phases are re-extracted with 3 l of dichloromethane and the organic phases are then combined, filtered and concentrated by distillation under reduced pressure. 496 g of product are obtained.

2.2. 3(S)-Methoxypropane-1,2-diol

A mixture of 496 g of product obtained in the preceding step is heated to 60° C., with stirring, in 220 ml of demineralized water, then 1.5 ml of 36% hydrochloric acid are added. The heating is maintained for 40 min, then the mixture is brought to pH 8–9 by addition of 19 ml of triethylamine. The solvent is evaporated under a pressure of 5.2 kPa at a temperature below 70° C. and then the residue is distilled at 61° C. under a pressure of 13 Pa. 246 g of product are obtained.
$[\alpha]_D^{20}=+5.8°$ (c=4; methanol).

2.3. 4(R)-Methoxymethyl-1,3-dioxolan-2-one

Into a round-bottomed flask equipped with a dropping funnel and a distillation assembly are introduced 245 g (3.31 mol) of 3(S)-methoxypropane-1,2-diol and 560 ml (4.62 mol) of diethyl carbonate. The mixture is heated to 95° C. and then a solution of sodium methoxide obtained starting from 10 ml of methanol and 0.5 g (0.02 mol) of sodium is added. The ethanol formed in the course of the reaction is distilled for 2 hours (bottom temperature: 95 to 112° C.; column temperature: 82 to 78° C.), then the mixture is cooled and distilled under a pressure of 13 Pa to separate the excess of diethyl carbonate. 267 g of product are obtained.
$[\alpha]_D^{20}=+30.3°$ (c=1; dichloromethane).

2.4. 3-[2-(3,3,3-Trifluoropropyl)benzofuran-5-yl]-5(S)-methoxymethyloxazolidin-2-one 1.2 g (4.0 mmol) of 5-ethoxycarbonylamino-2-(3,3,3-trifluoropropyl) benzofuran are treated with 4(R)-methoxymethyl-1,3-dioxolan-2-one under the conditions described in step 4 of Example 1; 0.98 g of product is obtained. Melting point: 80.2–80.3° C.
$[\alpha]_D^{20}=+36.5°$ (c=1; dichloromethane).

EXAMPLE 3

3-[2-(3,3,3-trifluoropropyl)benzofuran-5-yl]-5(R)-hydroxymethyloxazolidin-2-one

To a solution of 0.50 g (1.5 mmol) of 3-[2-(3,3,3-trifluoropropyl) benzofuran-5-yl]-5(R)-methoxymethyloxazolidin-2-one in 2 ml of dichloromethane are added dropwise, at −5° C., 2.5 ml (2.5 mmol) of a 1 M solution of boron tribromide in dichloromethane. The mixture is stirred for 2 hours at 0° C., then it is hydrolyzed by adding ammonia until the pH is basic. The product is then extracted with dichloromethane, and the organic phase is dried over sodium sulfate and concentrated under reduced pressure. By chromatography of the residue on a silica column with a 30% mixture of ethyl acetate in dichloromethane and trituration of the residue in diethyl ether, 0.23 g of product is obtained. Melting point: 150.7–150.8° C. $[\alpha]_D^{20}=-39.2°$ (c=1; dimethyl sulfoxide).

EXAMPLE 4

3-[2-propylbenzofuran-5-yl]-5(R)-methoxymethyloxazolidin-2-one 4.1. 5-Nitro-2-propylbenzofuran A suspension of 4.0 g (8.1 mmol) of (2-hydroxy-5-nitrophenyl) methyltriphenylphosphonium bromide in 50 ml of toluene is heated to reflux, then 3.4 ml (24 mmol) of triethylamine and 0.84 ml (8.1 mmol) of butyryl chloride are added. The mixture is stirred for 3 hours, then it is filtered and the filtrate is concentrated under reduced pressure. By chromatography of the residue on a silica column with a 0–50% mixture of dichloromethane in cyclohexane, 0.6 g of product is obtained in oil form.

4.2. 5-Amino-2-propylbenzofuran 1.4 g (6.8 mmol) of 5-nitro-2-propylbenzofuran are treated under conditions analogous to those of step 2 of Example 1. 0.9 g of product is obtained in oil form.

4.3. 5-Ethoxycarbonylamino-2-propylbenzofuran 0.90 g (5.1 mmol) of 5-amino-2-propylbenzofuran is treated under conditions analogous to those of step 3 of Example 1. 1.1 g of product are obtained. Melting point: 69–70° C.

4.4. 3-[2-Propylbenzofuran-5-yl]-5-(R)-methoxymethyloxazolidin-2-one 1.1 g (4.5 mmol) of 5-ethoxycarbonylamino-2-propylbenzofuran are treated with 4(S)-methoxymethyl-1,3-dioxolan-2-one under conditions analogous to those of step 4 of Example 1. After recrystallization in diisopropyl ether, 0.74 g of product is obtained. Melting point: 55.9° C.
$[\alpha]_D^{20}$=−43.1° (c=1; dichloromethane).

EXAMPLE 5

3-[2-phenylmethylbenzofuran-5-yl]-5(R)-methoxymethyloxazolidin-2-one 5.1. 2-Phenylmethyl-5-nitrobenzofuran 40 g (81 mmol) of (2-hydroxy-5-nitrophenyl)-methyltriphenylphosphonium bromide and 21.4 g (162 mmol) of phenylacetyl chloride are treated under the conditions described in step 1 of Example 1. 12 g of product are obtained. Melting point: 100° C.

5.2. 5-Amino-2-phenylmethylbenzofuran 10.8 g (42 mmol) of 2-phenylmethyl-5-nitrobenzofuran are treated under the conditions described in step 2 of Example 1. 9.1 g of product are obtained. Melting point: <50° C.

5.3. 5-Ethoxycarbonylamino-2-phenylmethylbenzofuran 9.1 g (41 mmol) of 5-amino-2-phenylmethylbenzofuran are treated under the conditions described in step 3 of Example 1. 11 g of product are obtained. Melting point: 95° C.

5.4. 3-[2-Phenylmethylbenzofuran-5-yl]-5(R)-methoxymethyloxazolidin-2-one 2.95 g (10.0 mmol) of 5-ethoxycarbonylamino-2-phenylmethylbenzofuran are treated with 4(S)-methoxymethyl-1,3-dioxolan-2-one under the conditions described in step 4 of Example 1. After recrystallization in diisopropyl ether, 2.0 g of product are obtained. Melting point: 99.4–99.7° C.
$[\alpha]_D^{20}$=−39.1° (c=1; dichloromethane).

EXAMPLE 6

3-[2-phenylbenzofuran-5-yl]-5(R)-methoxymethyloxazolidin-2-one 6.1. 5-Nitro-2-phenylbenzofuran 39 g (78 mmol) of (2-hydroxy-5-nitrophenyl) methyltriphenylphosphonium bromide and 18 ml (156 mmol) of benzoyl chloride are treated under conditions analogous to those of step 1 of Example 1. 15 g of product are obtained. Melting point: 159° C.

6.2. 5-Amino-2-phenylbenzofuran 15 g (63 mmol) of 5-nitro-2-phenylbenzofuran are treated under conditions analogous to those of step 2 of Example 1. 12.4 g of product are obtained. Melting point: 156° C.

6.3. 5-Ethoxycarbonylamino-2-phenylbenzofuran 12 g (58 mmol) of 5-amino-2-phenylbenzofuran are treated under conditions analogous to those of step 3 of Example 1. 16 g of product are obtained. Melting point: 164° C.

6.4. 3-[2-Phenylbenzofuran-5-yl]-5(R)-methoxymethyloxazolidin-2-one 3.1 g (11 mmol) of 5-ethoxycarbonylamino-2-phenylbenzofuran are treated with 4(S)-methoxymethyl-1,3-dioxolan-2-one under the conditions described in step 4 of Example 1. 2.5 g of product are obtained. Melting point: 178.5–179.3° C.
$[\alpha]_D^{20}$=−51.4° (c=1; dimethylformamide).

The compounds of the invention are compiled in the following table with their physical characteristics.

TABLE (I)

| No. | $R_1$ | $R_2$ | Config. | m.p.(° C.) | $[\alpha]_D^{20}$ (c = 1) | Solvent |
|---|---|---|---|---|---|---|
| 1 | $CF_3(CH_2)_2$ | $CH_3$ | 5(R) | 79.9–80.0 | −36.9° | dichloromethane |
| 2 | | | 5(S) | 80.2–80.3 | +36.5° | dichloromethane |
| 3 | $CF_3(CH_2)_2$ | H | 5(R) | 150.7–150.8 | −39.2° | dimethyl sulfoxide |
| 4 | $C_6H_5$—$CH_2$ | $CH_3$ | 5(R) | 99.4–99.7 | −39.1° | dichloromethane |
| 5 | | | 5(S) | 100.6 | +39.7° | dichloromethane |
| 6 | $C_6H_5$ | $CH_3$ | 5(R) | 178.5–179.3 | −51.4° | dimethylformamide |
| 7 | | | 5(S) | 178–179.1 | +50.4° | dimethylformamide |
| 8 | $C_6H_5$ | H | 5(R) | 219.4–219.5 | −45.4° | dimethyl sulfoxide |
| 9 | $CH_3(CH_2)_2$ | $CH_3$ | 5(R) | 55.9 | −43.1° | dichloromethane |

The compounds of the invention were the subject of pharmacological tests allowing their inhibitory power on monoamine oxidase A and monoamine oxidase B to be determined.

The measurements of the MAO-A and MAO-B activities in vitro were carried out using a rat brain homogenate as enzyme source, according to the method described by C. Fowler and M. Strolin-Benedetti, in J. Neurochem., 40, 1534–1541 (1983).

The standard determination consists in homogenizing the rat brain in 20 volumes of 0.1 M phosphate buffer (pH =7.4) and in preincubating 100 μl of homogenate (5 mg of tissue) at 37° C. for 20 minutes in the absence or in the presence of different concentrations of inhibitor studied. The reaction is started by the addition of [$^{14}$C]serotonin ([$^{14}$C]5 HT, final concentration 125 μM) for the measurement of the activity of MAO-A or of [$^{14}$C]phenylethylamine ([$^{14}$C]PEA, final concentration 8 μM) for the measurement of the MAO-B activity, in a final volume of 500 μl. After incubating for 5 minutes for [$^{14}$C]5 HT and incubating for 1 minute for [$^{14}$C]PEA, the reaction is stopped by addition of 200 μl of 4 N hydrochloric acid. The radioactive metabolites from the oxidative deamination are then separated from the nontransformed substrate by extraction into an organic phase, and quantified by counting the radioactivity. The inhibitory activities with respect to MAO-A and MAO-B are respectively given by the inhibition constants Ki (MAO-A) and Ki (MAO-B). For the compounds of the invention, the Ki (MAO-A) vary between 1.2 nM and values greater than 1000 nM and the Ki (MAO-B) between 22 nM and values greater than 1000 nM.

Certain compounds of the invention are selective inhibitors of MAO-A, it being possible for the Ki(MAO-B)/Ki (MAO-A) ratio to be greater than 200.

Others are mixed inhibitors of MAO-A and of MAO-B, it being possible for the ratio Ki(MAO-B)/Ki(MAO-A) to be between 0.1 and 10.

The results obtained show that the compounds of the invention can be used for the preparation of drugs which are selective inhibitors of MAO-A or mixed inhibitors of MAO-A and of MAO-B, these drugs finding employment in therapeutics, especially in the treatment of depressive states of all types, senile depressive psychoses, hypobulia, phobias, especially social phobias, humoral disorders, cognitive deficits connected with age, with dementias or with cerebrovascular or traumatic accidents, in the improvement of general cerebral performances, the prevention and the treatment of neurodegenerative diseases such as Parkinson's disease and Alzheimer's disease and all memory disorders, anxiety, panic attacks, in dependence and withdrawal treatment connected with the consumption of alcohol, tobacco and/or intoxicants, and loss of appetite.

The compounds of the invention can be present in association with at least one excipient, in the form of pharmaceutical compositions formulated with a view, especially, to administration by the oral, parenteral or rectal route, for example in the form of tablets, coated tablets, capsules, solutions, suspensions or suppositories.

By the oral, parenteral and rectal routes, the dose of active principle administered per day can vary between 1 and 100 mg/kg, in one or more administrations.

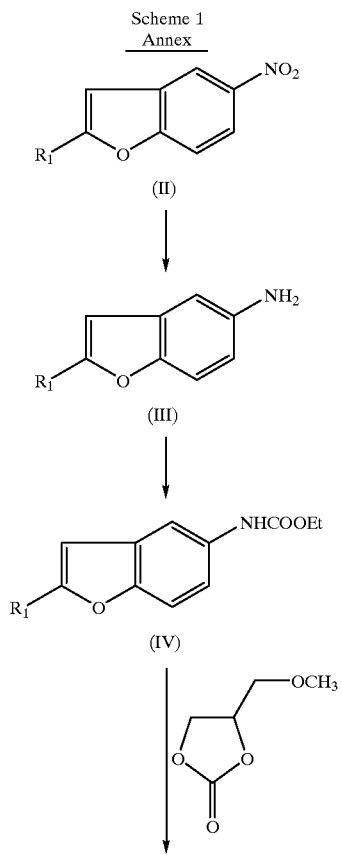

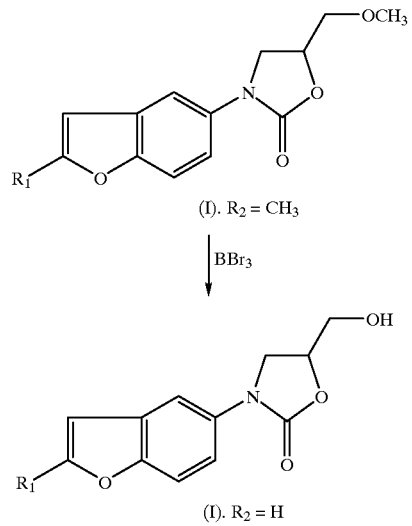

What is claimed is:

1. A compound of formula (I)

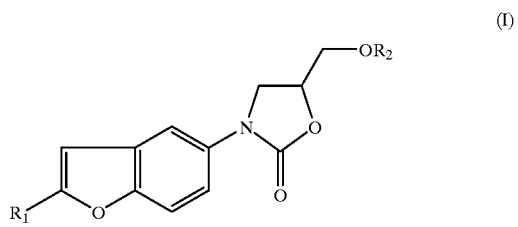

in which:
R$_1$ represents a phenyl group, a phenylmethyl group, an alkyl group comprising 3 to 6 carbon atoms or a fluoroalkyl group comprising 1 to 6 carbon atoms, and
R$_2$ represents a hydrogen atom or a methyl group.

2. A compound as claimed in claim 1, wherein R$_2$ represents a methyl group.

3. A compound as claimed in claim 1 wherein R$_1$ represents a phenyl group, a phenylmethyl group, a propyl group or a 3,3,3-trifluoropropyl group.

4. 3-[2-(3,3,3-Trifluoropropyl)benzofuran-5-yl]-5-methoxymethyloxazolidin-2-one and its enantiomers.

5. 3-(2-Propylbenzofuran-5-yl)-5-methoxymethyloxazolidin-2-one and its enantiomers.

6. 3-(2-Phenylbenzofuran-5-yl)-5-methoxymethyloxazolidin-2-one and its enantiomers.

7. A process for preparation of compounds of formula (I)

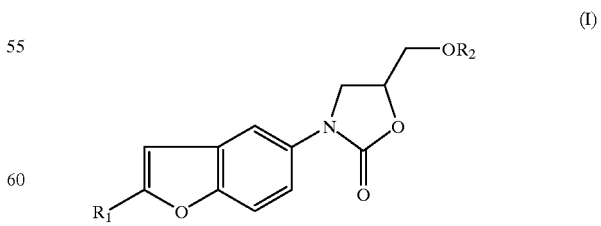

in which:
R$_1$ represents a phenyl group, a phenylmethyl group, an alkyl group comprising 3 to 6 carbon atoms or a fluoroalkyl group comprising 1 to 6 carbon atoms, and $R_2$ represents a hydrogen atom or a methyl group, which comprises reacting a compound of formula (IV)

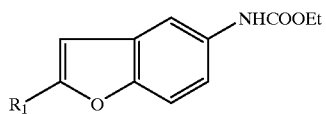

(IV)

where $R_1$ is as defined with respect to formula I, with 4-methoxymethyl-1,3-dioxolan-2-one to prepare the compounds of formula (I) where $R_2$ is a methyl group.

8. The process as claimed in claim 7, wherein the compound of formula (I) in which $R_2$ is a methyl group is treated with boron tribromide to obtain the compounds of formula (I) where $R_2$ is a hydrogen atom.

9. A pharmaceutical composition comprising a compound as claimed in claim 1 in combination with at least one appropriate excipient.

10. A method for the treatment of depression, phobias, anxiety and panic attacks, comprising administering to a patient in need thereof an effective amount of a compound of claim 1.

* * * * *